US012629270B2

(12) United States Patent
    Skelton

(10) Patent No.: US 12,629,270 B2
(45) Date of Patent: May 19, 2026

(54) CONSTRAINING MECHANISMS FOR SELECTIVE DEPLOYMENT AND ASSOCIATED METHODS

(71) Applicant: W. L. Gore & Associates, Inc., Newark, DE (US)

(72) Inventor: Tyson J. Skelton, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 809 days.

(21) Appl. No.: 17/609,861

(22) PCT Filed: May 10, 2019

(86) PCT No.: PCT/US2019/031780
    § 371 (c)(1),
    (2) Date: Nov. 9, 2021

(87) PCT Pub. No.: WO2020/231390
    PCT Pub. Date: Nov. 19, 2020

(65) Prior Publication Data
    US 2022/0211529 A1    Jul. 7, 2022

(51) Int. Cl.
    *A61F 2/97*      (2013.01)
    *A61M 25/10*     (2013.01)
    *D04B 21/20*     (2006.01)
(52) U.S. Cl.
    CPC .............. *A61F 2/97* (2013.01); *A61M 25/10* (2013.01); *D04B 21/205* (2013.01); *A61M 2025/1081* (2013.01); *D10B 2509/06* (2013.01)

(58) Field of Classification Search
    CPC ....................................................... A61F 2/97
    See application file for complete search history.

(56) References Cited

U.S. PATENT DOCUMENTS

| | | | |
|---|---|---|---|
| 4,878,906 A | 11/1989 | Lindemann et al. |
| 5,405,378 A | 4/1995 | Strecker |
| 5,671,790 A | 9/1997 | Andersen et al. |
| 6,224,627 B1 | 5/2001 | Armstrong et al. |
| 6,302,891 B1 | 10/2001 | Nadal |
| 6,315,792 B1 | 11/2001 | Armstrong et al. |
| 6,315,795 B1 | 11/2001 | Scarborough et al. |

(Continued)

FOREIGN PATENT DOCUMENTS

| | | |
|---|---|---|
| CA | 2456046 A1 | 12/1999 |
| CN | 201578402 U | 9/2010 |

(Continued)

OTHER PUBLICATIONS

Dictionary Definition of "Knot" Dictionary.com, https://www.dictionary.com/browse/knot. (Year: 2024).*

(Continued)

*Primary Examiner* — Andrew T Piziali

(57) ABSTRACT

Various aspects of the present disclosure are directed toward medical device deployment apparatuses, systems, and methods. The apparatuses, systems, and methods may include at least one constraining fiber configured to form a warp knit surrounding a medical device with a first series of loops forming the warp knit with at least one of the first series of loops including a first portion forming a knot and a second portion arranged in addition to the knot.

9 Claims, 5 Drawing Sheets

(56)  References Cited

U.S. PATENT DOCUMENTS

| | | |
|---|---|---|
| 6,352,553 B1 | 3/2002 | Van et al. |
| 6,514,281 B1 | 2/2003 | Blaeser et al. |
| 9,375,215 B2 | 6/2016 | Cully et al. |
| 9,427,307 B2 | 8/2016 | Pearson et al. |
| 9,439,791 B2 | 9/2016 | Vong et al. |
| 9,622,893 B2 | 4/2017 | Huser |
| 9,717,612 B2 | 8/2017 | Dorn et al. |
| 9,987,155 B1 | 6/2018 | Sondreaal |
| 2002/0045930 A1 | 4/2002 | Burg et al. |
| 2004/0122503 A1 | 6/2004 | Campbell et al. |
| 2004/0243215 A1 | 12/2004 | Nelson |
| 2005/0090890 A1 | 4/2005 | Wu et al. |
| 2007/0038310 A1 | 2/2007 | Guetty |
| 2007/0106364 A1 | 5/2007 | Buzzard et al. |
| 2008/0255580 A1 | 10/2008 | Hoffman et al. |
| 2009/0326640 A1 | 12/2009 | Yoshimura et al. |
| 2010/0011976 A1 | 1/2010 | Armstrong et al. |
| 2010/0030321 A1 | 2/2010 | Mach |
| 2010/0152829 A1 | 6/2010 | Edelman et al. |
| 2011/0218613 A1 | 9/2011 | Leopold et al. |
| 2012/0046652 A1 | 2/2012 | Sokel |
| 2012/0130475 A1 | 5/2012 | Shaw |
| 2012/0259406 A1 | 10/2012 | Schreck et al. |
| 2013/0123900 A1 | 5/2013 | Eblacas et al. |
| 2013/0245745 A1 | 9/2013 | Vong et al. |
| 2013/0289713 A1 | 10/2013 | Pearson et al. |
| 2014/0148895 A1 | 5/2014 | King |
| 2014/0180378 A1 | 6/2014 | Roeder |
| 2014/0200649 A1 | 7/2014 | Essinger et al. |
| 2014/0277363 A1 | 9/2014 | Armstrong et al. |
| 2015/0081000 A1 | 3/2015 | Hossainy et al. |
| 2015/0082595 A1 | 3/2015 | King |
| 2015/0173753 A1 | 6/2015 | Spivey et al. |
| 2015/0250630 A1 | 9/2015 | Irwin et al. |
| 2016/0199207 A1 | 7/2016 | Treacy et al. |
| 2017/0151079 A1 | 6/2017 | Shaw |
| 2017/0189212 A1 | 7/2017 | Eller et al. |
| 2017/0348099 A1 | 12/2017 | Mendelson et al. |
| 2018/0280171 A1 | 10/2018 | Gloss et al. |
| 2020/0368051 A1 | 11/2020 | Byrne et al. |
| 2021/0386567 A1 | 12/2021 | Stastka |
| 2021/0386569 A1 | 12/2021 | Stastka |
| 2022/0031485 A1 | 2/2022 | Ramirez et al. |
| 2022/0211528 A1 | 7/2022 | Skelton |
| 2022/0296399 A1 | 9/2022 | Broyles et al. |
| 2023/0099043 A1 | 3/2023 | Stastka |
| 2023/0225891 A1 | 7/2023 | Stastka |
| 2024/0299198 A1 | 9/2024 | Honeyfield |

FOREIGN PATENT DOCUMENTS

| | | |
|---|---|---|
| CN | 102088928 A | 6/2011 |
| CN | 103547235 A | 1/2014 |
| CN | 103945798 A | 7/2014 |
| CN | 105530895 A | 4/2016 |
| CN | 105899167 A | 8/2016 |
| CN | 106102596 A | 11/2016 |
| CN | 109688984 A | 4/2019 |
| EP | 0950385 A2 | 10/1999 |
| EP | 1087726 A1 | 4/2001 |
| EP | 2298248 A1 | 3/2011 |
| EP | 2735283 A1 | 5/2014 |
| EP | 2749251 B1 | 7/2016 |
| JP | 06-503734 A | 4/1994 |
| JP | 2000-503359 A | 3/2000 |
| JP | 2000-503559 A | 3/2000 |
| JP | 2002-518086 A | 6/2002 |
| JP | 2003-052833 A | 2/2003 |
| JP | 2005-270432 A | 10/2005 |
| JP | 2005-304792 A | 11/2005 |
| JP | 2006-510453 A | 3/2006 |
| JP | 2009-523565 A | 6/2009 |
| JP | 2010-526583 A | 8/2010 |
| JP | 2014-501563 A | 1/2014 |
| JP | 2018-501902 A | 1/2018 |
| JP | 2021-566524 A | 7/2022 |
| WO | 97/21402 A1 | 6/1997 |
| WO | 99/65420 A1 | 12/1999 |
| WO | 2007/084762 A2 | 7/2007 |
| WO | 2008/137177 A2 | 11/2008 |
| WO | 2009/140861 A1 | 11/2009 |
| WO | 2012/068046 A2 | 5/2012 |
| WO | 2016/115007 A1 | 7/2016 |
| WO | 2019/075069 A1 | 4/2019 |
| WO | 2019/240799 A1 | 12/2019 |
| WO | 2019/240800 A1 | 12/2019 |
| WO | 2020/068957 A1 | 4/2020 |
| WO | 2020/231387 A1 | 11/2020 |
| WO | 2021/173648 A1 | 9/2021 |

OTHER PUBLICATIONS

Dictionary Definition of "Knit" Dictionary.com, https://www.dictionary.com/browse/knit. (Year: 2024).*

"About Denier" https://standardfiber.com/about-denier (Year: 2012).

"What is Denier" https://www.onlinefabricstore.com/makersmill/what-is-denier/ (Year: 2012).

Merriam-Wester online dictionary, "knit" definition, accessed on Aug. 24, 2023, https://www.merriam-webster.com/dictionary/knit (Year: 2023) (Year: 2023).

International Preliminary Report on Patentability received for PCT Patent Application No. PCT/US2019/031761, mailed on Nov. 25, 2021, 9 pages.

International Preliminary Report on Patentability received for PCT Patent Application No. PCT/US2019/031769, mailed on Nov. 25, 2021, 10 pages.

International Preliminary Report on Patentability received for PCT Patent Application No. PCT/US2019/031780, mailed on Nov. 25, 2021, 7 pages.

International Preliminary Report on Patentability received for PCT Patent Application No. PCT/US2019/052921, mailed on Apr. 8, 2021, 8 pages.

International Preliminary Report on Patentability received for PCT Patent Application No. PCT/US2019/054630, mailed on Apr. 15, 2021, 9 pages.

International Preliminary Report on Patentability received for PCT Patent Application No. PCT/US2019/054652, mailed on Apr. 15, 2021, 8 pages.

International Search Report and Written Opinion received for PCT Patent Application No. PCT/US2019/031761, mailed on Jan. 22, 2020, 11 pages.

International Search Report and Written Opinion received for PCT Patent Application No. PCT/US2019/031769, mailed on Jan. 23, 2020, 16 pages.

International Search Report and Written Opinion received for PCT Patent Application No. PCT/US2019/031780, mailed on Jan. 20, 2020, 8 pages.

International Search Report and Written Opinion received for PCT Patent Application No. PCT/US2019/052921, mailed on Jan. 29, 2020, 13 pages.

International Search Report and Written Opinion received for PCT Patent Application No. PCT/US2019/054630, mailed on Jan. 29, 2020, 11 pages.

International Search Report and Written Opinion received for PCT Patent Application No. PCT/US2019/054652, mailed on Jan. 29, 2020, 9 pages.

International Search Report and Written Opinion received for PCT Patent Application No. PCT/US21/19386, mailed on Jun. 18, 2021, 12 pages.

International Search Report and Written Opinion received for PCT Patent Application No. PCT/US21/25919, mailed on Dec. 23, 2021, 20 pages.

Beute et al., "Use of EN Snare device for successful repositioning of the newest self-expanding transcatheter heart valve", SAGE, vol. 6, No. 1, Dec. 2018, pp. 1-3.

European Search Report for EP Patent Application No. 23170894.2, Issued on Oct. 20, 2023, 10 pages.

(56)           References Cited

OTHER PUBLICATIONS

International Preliminary Report on Patentability received for PCT Patent Application No. PCT/US2021/019386, mailed on Sep. 9, 2022, 9 pages.

International Preliminary Report on Patentability received for PCT Patent Application No. PCT/US2021/025919, mailed on Oct. 19, 2023, 13 pages.

International Preliminary Report on Patentability received for PCT Patent Application No. PCT/US2021/037311, mailed on Dec. 29, 2022, 8 pages.

International Search Report and Written Opinion received for PCT Patent Application No. PCT/US2021/037311, mailed on Sep. 30, 2021, 12 pages.

Lee et al., Sheath-assisted controlled deployment technique for Excluder bifurcated main body, Journal of Vascular Surgery, vol. 43, No. 5, May 2006, pp. 1060-1063.

Xiao-dong et al., "A patent analysis of biodegradable vascular scaffolds", Chinese Journal of Tissue Engineering Research, vol. 22, No. 2, 2018, pp. 303-309.

Zhang et al., "Application of Knitting Structure Textiles in Medical Areas", Autex Research Journal, vol. 18, No. 2, Jun. 12, 2018, pp. 1-11.

* cited by examiner

CONSTRAINING MECHANISMS FOR SELECTIVE DEPLOYMENT AND ASSOCIATED METHODS

CROSS-REFERENCE TO RELATED APPLICATION

This application is a national phase application of PCT Application No. PCT/US2019/031780, internationally filed on May 10, 2019, which is herein incorporated by reference in its entirety for all purposes.

FIELD

The present disclosure relates to apparatuses, systems, and methods that include constraints used in delivery of implantable medical devices. More specifically, the present disclosure relates to apparatuses, systems, and methods that include constraints for selective deployment of an expandable device during device delivery.

BACKGROUND

Stents and stent-grafts may be utilized to radially support a variety of tubular passages in the body, including arteries, veins, airways, gastrointestinal tracts, and biliary tracts. The preferred method of placing these devices has been to use specialized delivery systems to precisely place and deploy a device at the site to be treated. These delivery systems allow the practitioner to minimize the trauma and technical difficulties associated with device placements. Attributes of delivery systems include: low profile; ability to pass through introducer sheaths; ability to negotiate tortuous vasculature, smoothly and atraumatically; protection of constrained devices; and ability to accurately position and deploy the device.

Stents or stent-grafts may be deployed and plastically deformed, such as by using an inflatable balloon, or to self-expand, such as through elastic recovery, from a collapsed or constrained delivery diameter to an expanded and deployed diameter. Some stents are designed to elastically recover by being manufactured at their functional diameter out of a material that has elastic recovery properties, and then radially compressed to be mounted on a delivery catheter.

These stent and stent-graft devices may be held, compressed, or constrained in the delivery configuration prior to and during delivery to a target location.

SUMMARY

According to one example ("Example 1"), a medical device deployment apparatus includes at least one constraining fiber configured to form a warp knit surrounding a medical device, the warp knit being configured to separate and be removed to deploy the medical device; and wherein the at least one constraining fiber include a first series of loops forming the warp knit with at least one of the first series of loops including a first portion forming a knot and a second portion arranged in addition to the knot.

According to another example ("Example 2"), further to the apparatus of Example 1, the warp knit includes a second constraining fiber including a second series of loops and the first series of loops and the second series of loops form a knot row.

According to another example ("Example 3"), further to the apparatus of Example 2, the first portion of the series of loops and the second portion of the series of loops are arranged through the second series of loops.

According to another example ("Example 4"), further to the apparatus of Example 3, the second portion of the first series of loops includes a second loop.

According to another example ("Example 5"), further to the apparatus of Example 3, the second portion of the first series of loops includes a length of the at least one constraining fiber extending beyond a length of the at least one constraining fiber forming the knot.

According to another example ("Example 6"), further to the apparatus of Example 5, the length of the at least one constraining fiber is rotated relative to the knot.

According to another example ("Example 7"), further to the apparatus of Example 2, wherein each of the knots in the knot row are formed by the first series of loops and the second series of loops with each of the first series of loops including a second portion arranged in addition to the knots.

According to another example ("Example 8"), further to the apparatus of Example 1, the at least one of the first series of loops including the first portion forming the knot is arranged at a distal end of the warp knit.

According to another example ("Example 9"), further to the apparatus of Example 1, the at least one of the first series of loops including the first portion forming the knot is configured as to resist premature deployment of the medical device.

According to one example ("Example 10"), a method of releasably constraining a medical device includes forming a warp knit to surround a medical device using at least one constraining fiber, the warp knit being configured to separate and be removed to deploy the medical device and including a first series of loops; and forming a knot within the warp knit with at least one of the first series of loops including a first portion and a second portion arranged in addition to the knot.

According to another example ("Example 11"), further to the method of Example 10, forming the knot includes forming the knot at a distal end of the warp knit.

According to another example ("Example 12"), further to the method of Example 10, forming the knot includes forming a slip knot with the second portion being a length arranged in excess of the slip knot.

According to another example ("Example 13"), further to the method of Example 10, forming the knot includes forming the second portion in a second loop.

According to another example ("Example 14"), further to the method of Example 10, the knot is configured as to resist premature deployment of the medical device According to another example ("Example 15"), further to the method of Example 10, the warp knit includes a second constraining fiber including a second series of loops and the first series of loops and the second series of loops form a knot row.

According to one example ("Example 16"), a deployment apparatus includes an implantable medical device; a constraint configured to releasably constraint the implantable medical device in a constrained configuration, the constraint including: a first row of knots formed by a first constraining fiber interwoven with a second constraining fiber surrounding the medical device in the constrained configuration, and a second row of knots formed by the second constraining fiber interwoven with a third constraining fiber surrounding the medical device in the constrained configuration, the first row of knots including a distal knot formed by a first loop of the first constraining fiber and a second loop of the second constraining fiber with the second loop including a first portion forming the knot and a second portion arranged in addition to the knot.

According to another example ("Example 17"), further to the apparatus of Example 16, each of the knots in the second knot row are formed by a first series of loops and a second series of loops with each of the second series of loops including a first portion forming the knot and a second portion arranged in addition to the knots.

According to another example ("Example 18"), further to the apparatus of Example 16, the second portion includes a second loop.

According to another example ("Example 19"), further to the apparatus of Example 16, the distal knot is configured as to resist premature deployment of the medical device.

According to another example ("Example 20"), further to the apparatus of Example 16, the second portion includes a length of fiber extending beyond a length of the third constraining fiber forming the distal knot.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Definitions and Terminology

Figure 1:
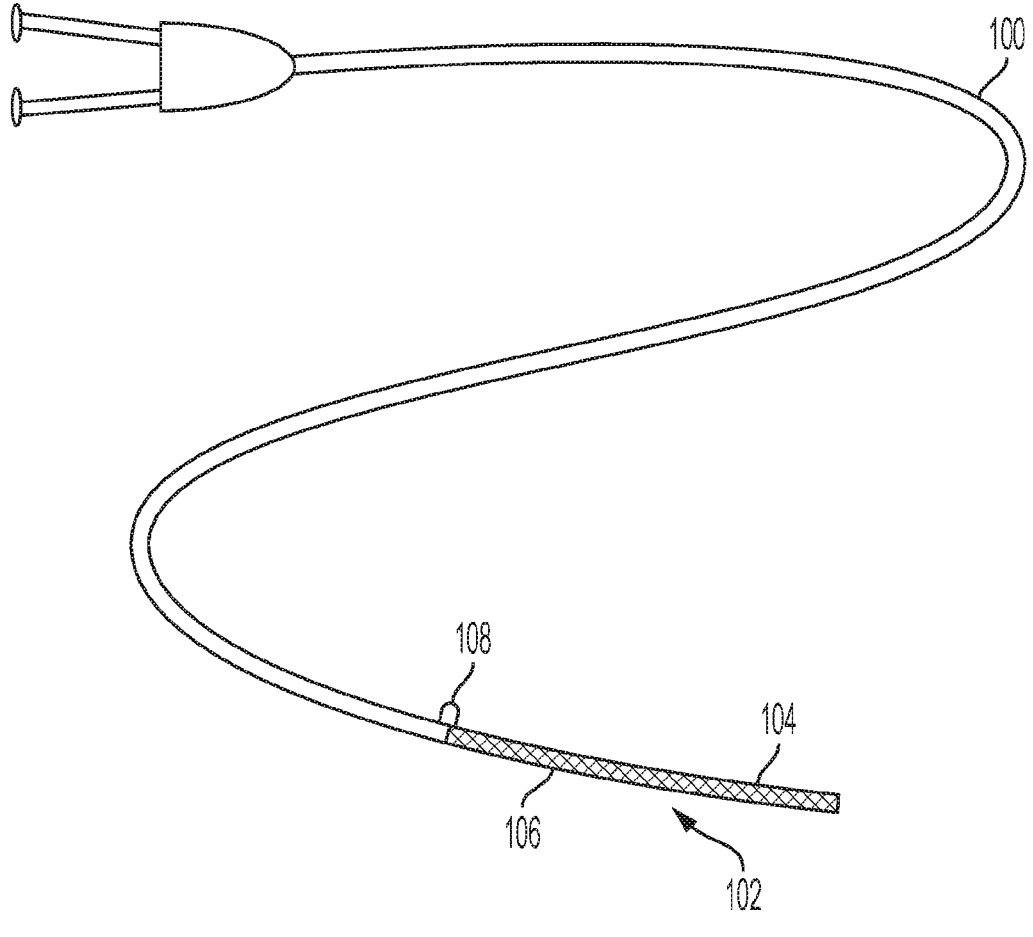
FIG. 1 is a top plan view of a delivery system including a catheter with a constraint, in accordance with an embodiment.

As the terms are used herein with respect to ranges of measurements "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

This disclosure is not meant to be read in a restrictive manner. For example, the terminology used in the application should be read broadly in the context of the meaning those in the field would attribute such terminology.

With respect terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

Certain terminology is used herein for convenience only. For example, words such as "top", "bottom", "upper," "lower," "left," "right," "horizontal," "vertical," "upward," and "downward" merely describe the configuration shown in the figures or the orientation of a part in the installed position. Indeed, the referenced components may be oriented in any direction. Similarly, throughout this disclosure, where a process or method is shown or described, the method may be performed in any order or simultaneously, unless it is clear from the context that the method depends on certain actions being performed first.

Description of Various Embodiments

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward apparatuses, systems, and methods that include forming or manufacturing a constraint. The constraining mechanisms are configured to hold, compress, or constraint an implantable medical device (e.g., a stent, stent-graft, balloon, filter, or other expandable medical device) in a delivery configuration prior to and during delivery to a target location. In certain instances, constraints may include one or more fibers that are arranged together. The fibers may be interwoven, stitched, or otherwise interlocked together circumferentially about the device. To remove the constraint, one or more of the fibers may be unknitted or disrupted from the other fibers in the constraint.

Constrained devices may store energy as a result of being constrained in a diameter smaller than a natural or deployed diameter. Thus, the devices may exhibit a radial displacement force against the constraint. During deployment of constrained devices, the radial force may force unknitting of the constraint without user involvement such that the constraint self un-knitts. The aspects of the present disclosure, however, eliminate this premature deployment. As discussed in further detail below, the constraint may include a pattern or knot structure that lessens premature deployment.

FIG. 1 is a top plan view of a catheter 100 with a constraint 102, according to some embodiments. As shown in FIG. 1, the constraint 102 is configured to constraint an implantable medical device 104 to a delivery configuration. The constraint 102 may include one or more fibers 106 arranged about the implantable medical device 104 to maintain the constraint 102 in a constrained configuration.

The constraint 102 is arranged along a length of the implantable medical device 104. The constraint 102 is also circumferentially arranged about the implantable medical device 104 and may substantially cover the implantable medical device 104 for delivery. The one or more fibers 106 may be arranged within a lumen (not shown) of the catheter 100 and extend toward a proximal end of the catheter 100 that is arranged external to a patient during delivery of the implantable medical device 104. The one or more fibers 106 include a proximal end 108 that a user may apply tension to in order to release the constraint 102 and deploy the implantable medical device 104.

In certain instances, the one or more fibers 106 release similar to a rip cord such that interlocking portions (e.g., overlapping fibers or knots) sequentially release along the length of the implantable medical device 104. As is explained in greater detail below, the constraint 102 is formed by interlocking together the one or more fibers 106 directly on the implantable medical device 104. The constraint 102 may be knitted together and then subsequently arranged about a constrained device or the constraint 102 is formed directly on the implantable medical device 104. The expandable medical device 104 may be a stent, stent-graft, a balloon, or a similar device.

Figure 2:
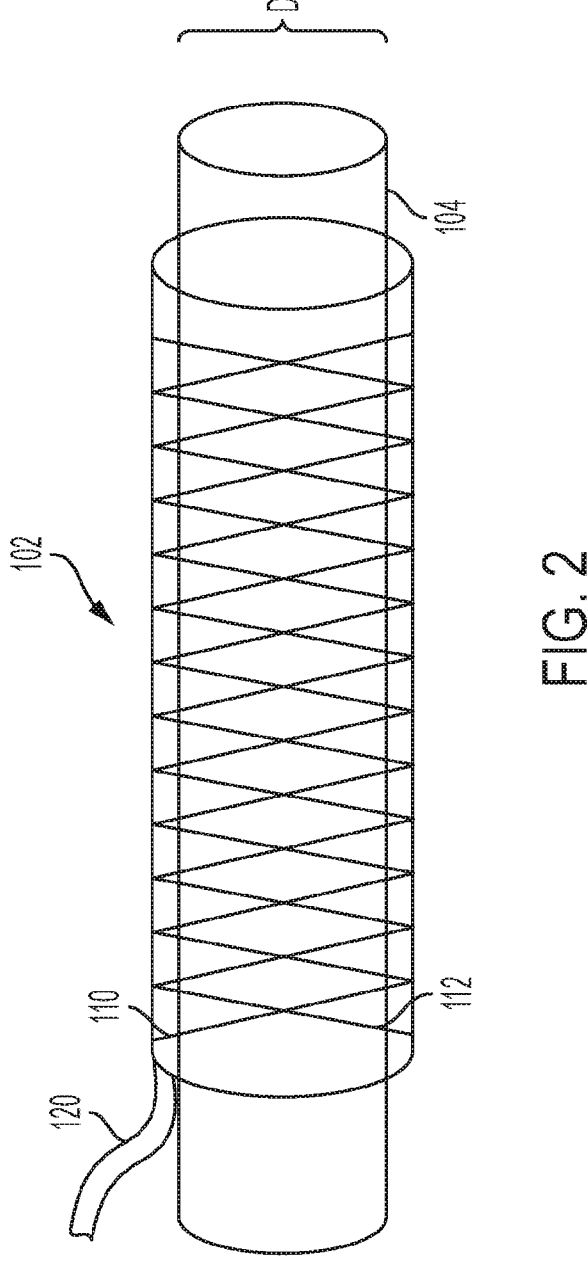
FIG. 2 is a side view of an implantable medical device including a constraint, in accordance with an embodiment.

FIG. 2 is a side view of the device 104 including the constraint 102, in accordance with an embodiment. As shown, the device 104 includes a delivery diameter D1 and a deployed diameter D2 (not shown) that is larger than the delivery diameter D1. The removable constraint 102 is attached to the device 104 at its delivery diameter D1. As shown, the constraint 102 includes at least two constraining fibers in the form of a warp knit. For example, the constraint 102 may include a first constraining fiber 110 and a second constraining fiber 112. The first and/or the second constraining fiber(s) 110, 112 may operate, for example, as a deployment line 120 configured to release the constraint 102 and transition the device 104 from the delivery diameter D1 to the deployed diameter D2 in response to a force applied to the deployment line 120 (which may be coupled to one or more of the knot rows 114 as discussed in further detail below).

The device 104 may have a desired deployed diameter D2 from about 5 mm-15 mm, or 6 mm-9 mm, or 6 mm-12 mm, 10 mm-20 mm, 15 mm-30 mm, 25 mm-45 mm, for example, and a delivery diameter D1 that is less than the deployed diameter D2. For example, in some instances, a ratio of the delivery diameter D1 of the device 104 to the deployed diameter D2 (not shown) of the device 104 is less than about 0.3, less than about 0.29, less than about 0.28, less than about 0.27, or less than about 0.26. For reference, the term "diameter" is not meant to require a circular cross-section, and is instead to be understood broadly to reference a maximum transverse cross-sectional dimension of a device 104.

Figure 3:
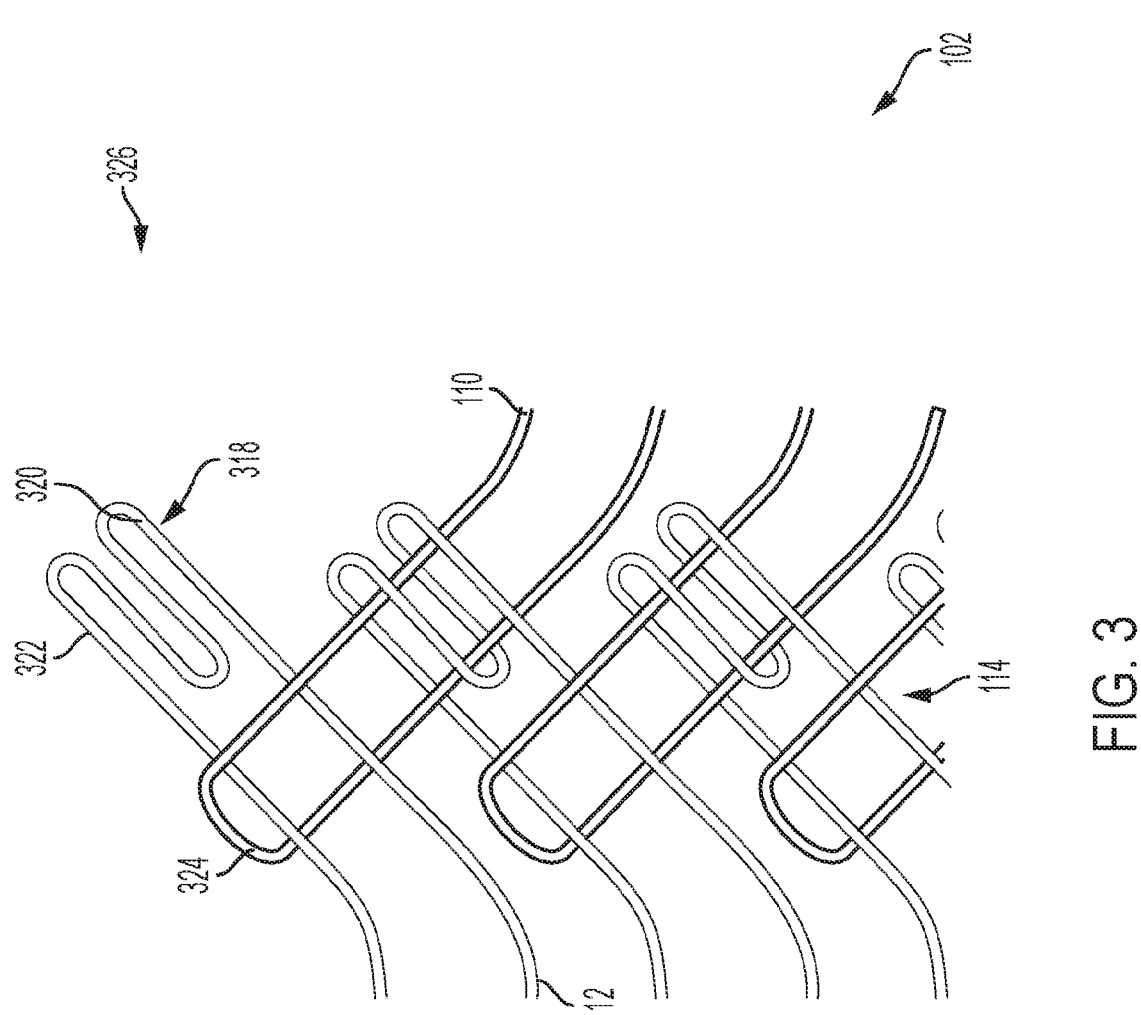
FIG. 3 is an illustration of an example deployment apparatus, in accordance with an embodiment.

FIG. 3 is an illustration of an example deployment apparatus, in accordance with an embodiment. FIG. 3 shows aspects of the deployment apparatus including at least one constraining fiber 110. In certain instances, the at least one constraining fiber 110 is looped onto itself to form a knit row 114. In other instances, the at least one constraining fiber 110 includes a first constraining fiber 110 and a second constraining fiber 112. For ease of illustration, the description of FIG. 3 will refer to the first constraining fiber 110 and the second constraining fiber 112.

In certain instances, the at least one constraining fiber 100 is arranged configured to form a warp knit surrounding a medical device. The warp knit is configured to separate and be removed to deploy the medical device. In addition, the at least one constraining fiber 100 may include a first series of loops forming the warp knit with at least one of the first series of loops 318 (one highlighted for ease of illustration) including a first portion 320 forming a knot 326 and a second portion 322 arranged in addition to the knot 326.

In certain instances, the first constraining fiber 110 and the second constraining fiber 112 may form a constraint 102. At a distal end of the constraint 102 (e.g., at a distal end of the knot row 114), the distal knot 326 may be formed by loops of the at least one constraining fiber 110 (or the first constraining fiber 110 and the second constraining fiber 112). In certain instances, the second constraining fiber 112 including a second series of multiple loops 324 (one highlighted for ease of illustration) and the first series of loops 318 and the second series of loops 324 form the knot row 114.

As shown in FIG. 3, the first portion 320 of the series of loops 318 and the second portion 322 of the series of loops 318 are arranged through the second series of multiple loops 324. The first portion 320 and the second series of multiple loops 324 may form knots in the knot row 114. In certain instances, the distal knot 326 may include the first portion 320 of the series of loops 318 and the second portion 322 of the series of loops 318 with remaining knots in the knot row 114 not including the excess length of the second portion 322 of the series of loops 318. For example, the first portion 320 of the series of loops 318 is of a length to form a knot with the second series of multiple loops 324. The additional length provided by the second portion 322 of the series of loops 318 (in addition to the length for forming a knot) requires additional displacement of constraining fiber material to unknit the knot 326. The additional displacement facilitates and resists premature deployment of the constraint 102. In response to tension applied to a deployment line or the at least one constraining fiber 110, the warp knit un-knits. The additional length provided by the second portion 322 of the series of loops 318 increases friction within needed to un-knit the knot 326 (or multiple knots in the knot row 114 having the additional length provided by the second portion 322 of the series of loops 318), which resists premature deployment.

In certain instances, the second portion 322 of the series of loops 318 includes a second loop with the first portion 318 being a first loop. In certain instances, the second portion 322 of the series of loops 318 (or the length in addition to the knot 326) is rotated or twisted relative to the knot 326. In addition, the first series of loops 318 including the first portion 320 which form the knot 326 may be configured as to resist premature deployment of the medical device.

Figure 4:
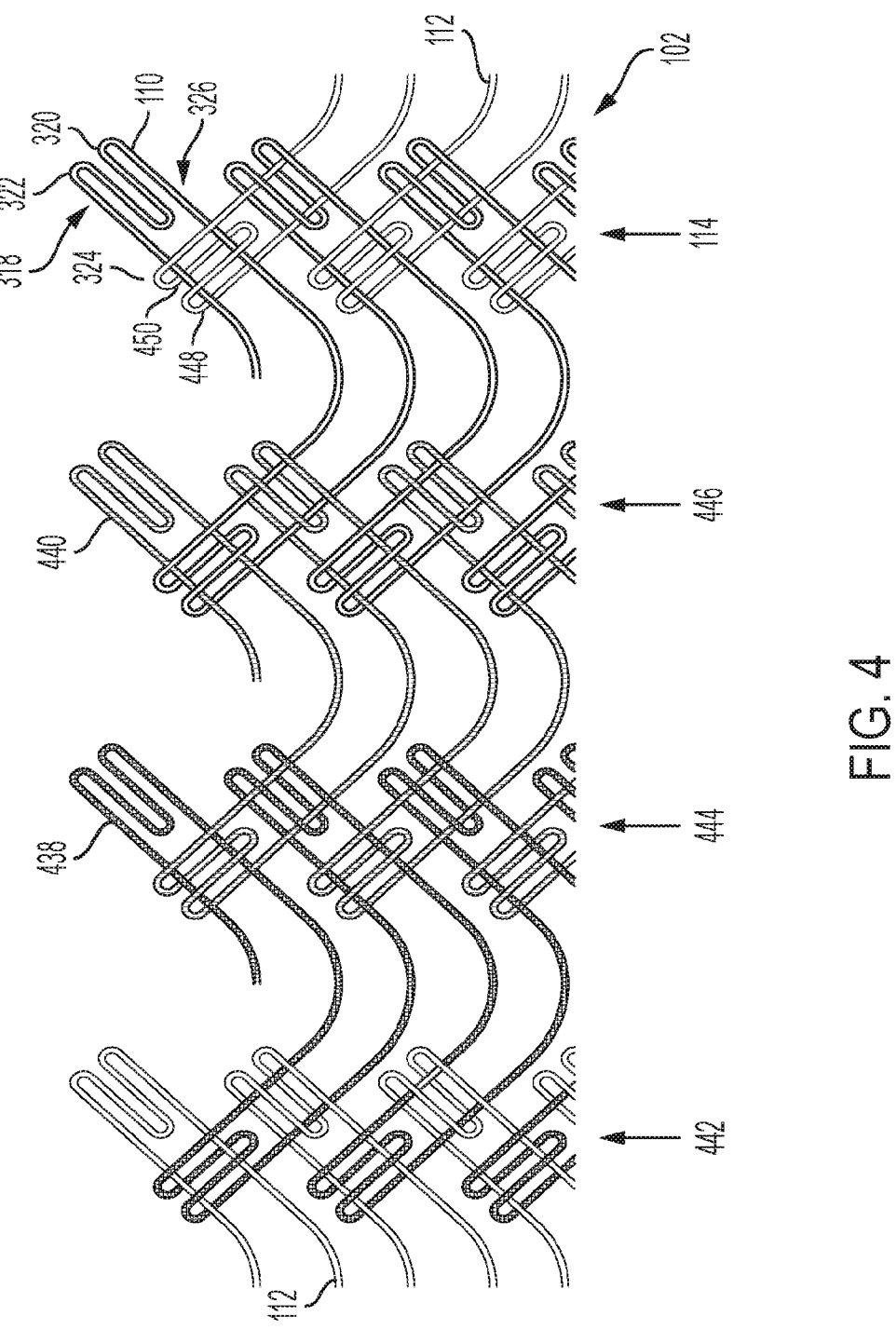
FIG. 4 is an illustration of an example deployment apparatus, in accordance with an embodiment.

FIG. 4 is an illustration of an example deployment apparatus, in accordance with an embodiment. The constraint 102 is shown as a sheet of interwoven fibers, however, the constraint 102 may be arranged circumferentially about an implantable medical device. The constraint 102 can include a first constraining fiber 110 and a second constraining fiber 112 as described above with reference to FIG. 3. For example and as shown in FIG. 4, the constraint 102 includes a first constraining fiber 110, a second constraining fiber 112, a third constraining fiber 438, and a fourth constraining fiber 440. The constraining fibers 110, 112, 438, 440 may be arranged together to form multiple knot rows 114, 442, 444, 446. In certain instances, the number of constraining fibers 110, 112, 438, 440 may be equal to the number of knot rows 114, 442, 444, 446. In addition, the constraining fibers 110, 112, 438, 440 may be interwoven or interlocked with one another to form the knot rows 114, 442, 444, 446.

In certain instances, the first row of knots 114 of the constraint 102 may be formed by the first constraining fiber 110 interwoven with the second constraining fiber 112. As shown, the first constraining fiber 110 are interwoven with the second constraining fiber 112 to form the knot row 114 in a warp knit.

In addition, the second row of knots 442 may be formed by the second constraining fiber 112 interwoven with the third constraining fiber 438. The second constraining fiber 112 may be interwoven with the third constraining fiber 438 to form the row of knots 442. Further, the third row of knots 444 may be formed by the third constraining fiber 438 interwoven with the fourth constraining fiber 440, and the fourth row of knots 446 may be formed by the fourth constraining fiber 440 interwoven with the first constraining fiber 110.

In certain instances, each of the knot rows 114, 442, 444, 446 may be a warp knit when the constraint 102 is surrounding the medical device in the constrained configuration. As described above with reference to FIG. 3, the constraint 102 may be formed by one or more constraining fiber 110. To deploy the constraint 102 from the constrained configuration, tension may be applied to one of the constraining fibers 110. In certain instances, a knot 326 may be formed within the warp knit with at least one of a first series of loops 318 including a first portion 320 and a second portion 322 arranged in addition to the knot 326. In certain instances, the knot 326 may be at a distal end of the constraint 102 or knot row 114. The knot 326, and all knots in the knot row 114, may be formed with loops 324 (one highlighted for ease of illustration) formed by the second constraining fiber 112.

In certain instances, the second series of loops 324 of the second constraining fiber 112 may also include a first portion 448 and a second portion 450 arranged in addition to the knot 326. Each of the second portions 322, 450 may include a length of the constraining fibers 110, 112 that extend beyond a length of the constraining fibers (e.g., first portions 320, 448) forming the knot 326. In certain instances, the second series of loops 324 may be a single loop as shown in FIG. 3. In addition, each knot in the knot row 114 may include the additional length second portions 322, 450. In other instances, only the first constraining fiber 110 or the second constraining fiber may include the additional length second portions 322, 450.

In certain instances, the knots 326 may be a slip knot. In addition, the knot 326 or knots may be configured as to resist premature deployment of the medical device. Further, the other knot rows 442, 444, 446 may be similarly configured to include excess length in addition to the knots of the knot rows 442, 444, 446.

The warp knit pattern of the constraint 102 shown in FIG. 4 (which may include a single knot 326, multiple knots of a single knot row 114, single distal knots 326 in multiple knot rows 114, 442, 444, 446, or multiple knots in multiple knot rows 114, 442, 444, 446 with second portions or excess length) reduces premature deployment or mis deployment when the constraint 102 is un-knit. The excess length or longer loops, for example, require additional displacement in order to un-knit them. The longer loops are created by doubling the loop around the previously created loop of a knot in the knot rows 114, 442, 444, 446. Once a loop is un-knitted from the double loop, it may be become a twisted loop that can also be un-kitted. In order to un-knit the twisted loop, the loop must be pulled further than a loop made with a single loop. That additional length required to pull the double loop out may require additional circumferential displacement in order to self un-knit the construct and therefore reduce the potential for premature deployment (e.g., self un-kitting or accelerated deployment).

Figures 5A, 5B:
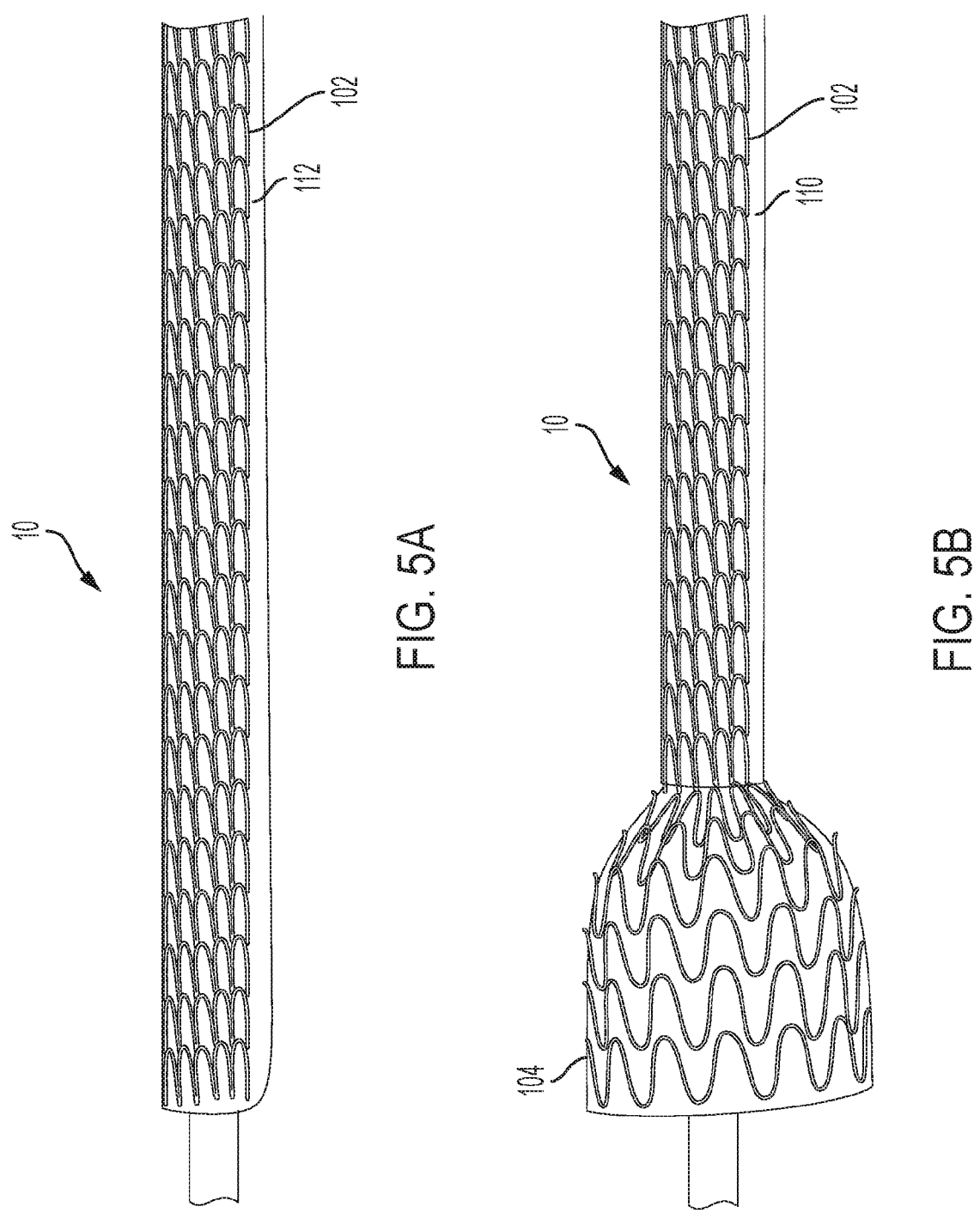
FIG. 5A is an image of a delivery system in a delivery configuration, in accordance with an embodiment.
FIG. 5B is an image of the delivery system, shown in FIG. 5A, in a semi-deployed configuration, in accordance with an embodiment.

FIG. 5A is an image of a delivery system 10 in a delivery configuration, in accordance with an embodiment. FIG. 5B is an image of a delivery system 10 in a semi-deployed configuration, in accordance with an embodiment. As shown, disrupting one of the constraining fibers (e.g., the second constraining fiber 112, for example) of a knot row initiates unravelling of at least a portion of the constraint 102, as shown in FIG. 5B.

The inventive concepts of this application have been described above both generically and with regard to specific embodiments. It will be apparent to those skilled in the art that various modifications and variations can be made in the embodiments without departing from the scope of the disclosure. Thus, it is intended that the embodiments cover the modifications and variations of the inventive concepts provided they come within the scope of the appended claims and their equivalents.

What is claimed is:

1. A medical device deployment apparatus, the apparatus comprising:

at least one constraining fiber defining a warp knit surrounding a medical device, the warp knit being configured to separate and be removed to deploy the medical device; and wherein the at least one constraining fiber includes a first constraining fiber including a first series of loops and a second constraining fiber including a second series of loops forming the warp knit, wherein a first loop of the first series of loops includes a first portion forming a knit and a second portion arranged in addition to the knit, wherein a second loop of the second series of loops is arranged through the first portion of the first loop of the at least one of the first series of loops and interwoven through the second portion of the first loop of the at least one of the first series of loops.

2. The apparatus of claim 1, wherein the warp knit includes a second constraining fiber including the second series of loops and the first series of loops and the second series of loops form a knit row.

3. The apparatus of claim 2, wherein the first portion of the series of loops and the second portion of the series of loops are arranged through the second series of loops.

4. The apparatus of claim 3, wherein the second portion of the first series of loops includes a second loop.

5. The apparatus of claim 3, wherein the second portion of the first series of loops includes a length of the at least one constraining fiber extending beyond a length of the at least one constraining fiber forming the knit.

6. The apparatus of claim 5, wherein the length of the at least one constraining fiber is rotated relative to the knit.

7. The apparatus of claim 2, wherein each of the knits in the knit row are formed by the first series of loops and the second series of loops with each of the first series of loops including a second portion arranged in addition to the knits.

8. The apparatus of claim 1, wherein the at least one of the first series of loops including the first portion forming the knit is arranged at a distal end of the warp knit.

9. The apparatus of claim 1, wherein the at least one of the first series of loops including the first portion forming the knit is configured as to resist premature deployment of the medical device.

\*   \*   \*   \*   \*